(12) United States Patent
Wakamatsu et al.

(10) Patent No.: US 7,554,247 B2
(45) Date of Patent: Jun. 30, 2009

(54) COMPONENT MEASURING DEVICE

(75) Inventors: Shunichi Wakamatsu, Sayama (JP);
Tsuyoshi Shiobara, Sayama (JP);
Tsukasa Kobata, Sayama (JP); Naoki Onishi, Sayama (JP)

(73) Assignee: Nihon Dempa Kogyo Co., Ltd, Tokyo (JP)

( * ) Notice: Subject to any disclaimer, the term of this patent is extended or adjusted under 35 U.S.C. 154(b) by 0 days.

(21) Appl. No.: 11/792,965

(22) PCT Filed: Dec. 14, 2005

(86) PCT No.: PCT/JP2005/023418

§ 371 (c)(1),
(2), (4) Date: Jun. 13, 2007

(87) PCT Pub. No.: WO2006/064952

PCT Pub. Date: Jun. 22, 2006

(65) Prior Publication Data

US 2008/0129148 A1    Jun. 5, 2008

(30) Foreign Application Priority Data

Dec. 15, 2004   (JP)   .............................. 2004-363539

(51) Int. Cl.
*H01L 41/053*    (2006.01)
(52) U.S. Cl. .................................. 310/344; 310/323.21
(58) Field of Classification Search ................. 310/344, 310/348, 312, 323.21; 324/633
See application file for complete search history.

(56) References Cited

U.S. PATENT DOCUMENTS 4,991,283 A    2/1991   Johnson et al.

(Continued)

FOREIGN PATENT DOCUMENTS

JP    1-244335    9/1989

(Continued)

*Primary Examiner*—Quyen Leung
*Assistant Examiner*—Derek J Rosenau
(74) *Attorney, Agent, or Firm*—Jordan and Hamburg LLP

(57) ABSTRACT

An object of the present invention is to perform measuring work easily when detecting the presence or absence of an object to be measured or the concentration thereof using a plurality of quartz sensors equipped with a Langevin type quartz resonator. As a concrete means for solving the problem, a quartz sensor 3 equipped with a quartz resonator 30 forming an adsorbing layer to adsorb a target component to be measured on one surface side and coming into contact with an airtight space on the other surface side is installed in a printed circuit board 4 via a base 5. A plurality of quartz sensors 3 is detachably installed respectively in a plurality of connecting terminal units provided in a horizontal arrangement on a side surface 21 of the measuring device main unit 2 via a connecting terminal unit 41 formed on an end of the printed circuit board 4 in a state that the above-described adsorbing layer faces upward. The measuring device main unit 2 includes an oscillation circuit 71 electrically connected to the quartz sensor 3, detects the variation of the natural frequency of the quartz resonator due to coming the sample solution into contact with the above-described adsorbing layer, and measures at least one of the presence of the target component to be measured or the concentration of the target component in the sample solution based on the detection result.

20 Claims, 10 Drawing Sheets

U.S. PATENT DOCUMENTS

| | | | |
|---|---|---|---|
| 5,196,347 | A | 3/1993 | Kaneko et al. |
| 5,494,639 | A | 2/1996 | Grzegorzewski |
| 5,892,143 | A | 4/1999 | Namerikawa et al. |
| 6,210,226 | B1 | 4/2001 | Zhu et al. |
| 6,321,588 | B1 | 11/2001 | Bowers et al. |
| 6,525,549 | B1 * | 2/2003 | Poellmann ................. 324/717 |
| 6,938,462 | B2 | 9/2005 | Jakoby et al. |
| 7,036,375 | B2 * | 5/2006 | Nozaki ....................... 73/579 |
| 7,046,096 | B2 | 5/2006 | Kobayashi |
| 7,055,377 | B2 | 6/2006 | Paul et al. |
| 2004/0016297 | A1 | 1/2004 | Paul et al. |
| 2004/0187580 | A1 | 9/2004 | Nozaki |
| 2005/0052813 | A1 | 3/2005 | Kobayashi |
| 2006/0141608 | A1 * | 6/2006 | Aastrup et al. ........... 435/287.1 |
| 2008/0047331 | A1 | 2/2008 | Wakamatsu et al. |
| 2008/0129148 | A1 | 6/2008 | Wakamatsu et al. |
| 2008/0134767 | A1 | 6/2008 | Wakamatsu et al. |
| 2008/0156097 | A1 | 7/2008 | Onishi et al. |

FOREIGN PATENT DOCUMENTS

| | | |
|---|---|---|
| JP | 3-257346 | 11/1991 |
| JP | 4-1554 | 1/1992 |
| JP | 4-9744 | 1/1992 |
| JP | 5-5735 | 1/1993 |
| JP | 7-190916 | 7/1995 |
| JP | 9-145583 | 6/1997 |
| JP | 9-250936 | 9/1997 |
| JP | 10-142134 | 5/1998 |
| JP | 10-332463 | 12/1998 |
| JP | 11-183479 | 7/1999 |
| JP | 2000-338022 | 12/2000 |
| JP | 2001-83154 | 3/2001 |
| JP | 2001-099777 | 4/2001 |
| JP | 2001-201436 | 7/2001 |
| JP | 2002-148295 | 5/2002 |
| JP | 2002-243607 | 8/2002 |
| JP | 2004-205392 | 7/2004 |
| JP | 2004-264254 | 9/2004 |
| JP | 2004-340766 | 12/2004 |
| JP | 2005-43123 | 2/2005 |

* cited by examiner

COMPONENT MEASURING DEVICE

TECHNICAL FIELD

The present invention relates to a component measuring device for measuring a target component in a sample solution, using a quartz sensor which is composed such that one surface of a quartz resonator comes in contact with a sample solution and the other surface faces an airtight space to sense the measurement target component by detecting the variation of frequencies.

BACKGROUND ART

A quartz sensor utilizing a quartz resonator to sense a substance in minute quantity such as an environmental pollutant or a disease marker is widely known, and a technology in, for instance, Patent Document 1 proposes a disease marker measuring device using such a quartz sensor. The disease marker measuring device includes, as shown in FIG. 14, a means to capture a disease maker substance by a latex aggregation reaction (latex aggregation reaction vessel) 11, a means to stick the captured disease marker substance to the quartz resonator (quartz resonator) 12, and a means to oscillate the quartz resonator to which the disease marker substance sticks and to measure and display the deviation of the oscillating frequency (detector main unit) 13.

A means to oscillate the quartz resonator to which the disease marker substance (oscillation circuit) 14, a means to measure the variation of frequency occurred by the oscillation of the quartz resonator (frequency meter) 15, and a means to display the measured frequency (display for oscillation frequency) 16 are installed and integrated in the inside of the detector main unit. The quartz resonator 12 are integrated with the oscillation circuit 14 and a battery in the detector main unit 13 and enclosed in metal box.

In such a device, an immuno-latex solution is filled in the latex aggregation reaction vessel 11 (reaction cell), one surface of the quartz resonator 12 is immersed in a reaction cell, and the oscillation frequency thereof is stabilized. Next, a solution containing a measurement target antigen is added into the reaction vessel 11, the disease marker substance is captured by the latex aggregation reaction, and frequency difference before and after addition of the antigen is calculated 60 minutes after completion of the immuno-latex aggregation. Thus, the measurement of concentration of the target is conducted.

Incidentally, a measurement device utilizing a quartz sensor sometimes shows a slight deviation in the frequency of the quartz sensor due to fluctuation in the manufacturing process. In order to perform high accuracy measurement, it is preferable that a plurality of, for instance 8 pieces of quartz sensors having the same structure are prepared, whereas 8 kinds of sample solutions different in the dilution ratio of the sample to be measured are prepared, the concentrations of the sample in 8 kinds of sample solutions different in the dilution ratio are measured by the respective 8 pieces of quartz sensors, and a calibration curve is prepared from respective concentrations thus obtained to determine the concentration.

When this technology is applied to a disease marker measurement device in Patent Document 1, however, in order to measure the concentration of a sample solution, 8 pieces of the quartz resonators 12 (quartz sensor) are required to be connected to the detector main unit 13. In the device described in the Patent Document 1, only one quartz resonator 12 can be connected to the detector main unit 13, and although an electrical connection diagram between the quartz resonator 12 and the detector main unit 13 is described, a concrete method of connection is not described. Accordingly, to what extent the operator working for the measurement will be inconvenienced by having to attach and detach the quartz resonator is not yet known, but if 8 times of measuring work is conducted, each occasion will require attachment and detachment, thus causing a problem of making the measuring work burdensome. Furthermore, there is a further problem in that since it takes about 60 minutes for measuring one sample, it takes a long time to finish the whole measurement.

In the technology disclosed in Patent Document 1, the measuring work is conducted in a manner that the quartz resonator 12 immersed in the latex aggregation reaction vessel 11 and the detector main unit 13 are connected on a working bench. Therefore when the quartz resonator 12 and the detector main unit 13 are connected through a lead wire, the wiring is routed around the work bench. This may cause snagging of this wiring and upsetting of the reaction vessel 11 in which the quartz resonator 12 is immersed.

Patent Document 1

Japanese Patent Application Laid-open No. 2001-83154 (refer to paragraphs 0007, 0012, 0017 and FIG. 1)

DISCLOSURE OF THE INVENTION

The present invention has been achieved in consideration of these circumstances, and an object thereof is to provide a component measuring device which can conduct measuring work to detect the presence of a target component or concentration of the target component easily and in a short time by providing a plurality of quartz sensor detachably to a measuring device main unit.

A component measuring device relating to the present invention used for detecting a target component to be detected in a sample solution, including:

a quartz sensor including a holding unit provided with a recess for forming an airtight space, and a quartz resonator which has an adsorbing layer to adsorb a measurement target component being formed on an excitation electrode on one surface side and which is held by said holding unit in a state that an excitation electrode on the other surface side covers the recess so as to face said recess;

a measuring device main unit including an oscillation circuit electrically connected to the quartz sensor and detecting the variation of the natural frequency of the quartz resonator caused by making the sample solution come in contact with the above-described adsorbing layer; and a plurality of connecting terminal units, provided in the measuring device main unit, and detachably attached by a plurality of quartz sensors in a state that the above-described adsorbing layer faces upward, in which at least one of the presence/absence of the target component or the concentration of the target component in the sample solution is determined based on the detection result in the above-described measuring device main unit.

A plurality of the connecting terminal units of the measuring device main unit is provided, for instance, in a manner that quartz sensors are horizontally arranged. A lid may be provided to cover the surrounding of the quartz sensor installed in the measuring device main body. In this case, it is preferable that the lid is rotatable around an axis horizontally extending along the side face of the measuring device main unit, and is formed to be able to open and close between the position covering a plurality of the quartz sensors and the position where the quartz sensor is exposed so that the sample solution can be poured into the measuring device. In addition, the lid may be formed so that the area covered by the lid can be shielded from the external environment. It is also accepted that the lid is formed such that the inside of the lid is divided into two or more so as to independently cover the plural quartz sensors and the divided areas are shielded from each other.

The above-described holding unit may be formed to have, for instance, a circuit board provided with a connecting terminal unit to be attached to a connecting terminal unit of the measuring device main unit at an end thereof. In addition, the holding unit may be provided with a quartz holding member made of an elastic material stacked on the circuit board and the quartz resonator may be attached to the quartz holding member. The excitation electrode of the quartz resonator and the electrode of the circuit board may be adhered by a conductive adhesive with each other.

According to the present invention, it is formed such that a plurality of quartz sensors provided with Langevin type quartz resonators is detachably connected to the measuring device main unit in a manner that the adsorbing layer faces upward. Therefore, it is possible to conduct a work to drop, for instance, a sample solution on a plurality of quartz sensors and to measure with ease. Furthermore, since no wiring for connecting between the quartz sensor and the measuring device main unit is routed on a work bench, there is no fear that the quartz sensor falls due to getting the wiring snagged on, which result in improvement of workability also from this point of view. Further, since the measurement work can be performed in parallel using a plurality of quartz sensors, drastic reduction in the period of time required for the measurement can be realized compared with the case of the measurement work plural times using one piece of the quartz sensor. In addition, the inclusion of a lid to cover the quartz sensor ensures that there is no fear of dust contamination or the like of the quartz sensor in the atmosphere where the measuring device main unit is placed. Further, by forming the area covered by the lid so as to be shielded from the external environment, the quartz sensor becomes resistant to be influenced by the electromagnetic waves. Still further, by dividing the lid into two or more so as to cover the plural quartz sensors independently, and by forming the respective divided areas so as to be shielded from each other, the influence from frequencies of the adjacent quartz sensors is reduced so that measurement with high accuracy can be realized.

BEST MODE FOR CARRYING OUT THE INVENTION

Figure 1:
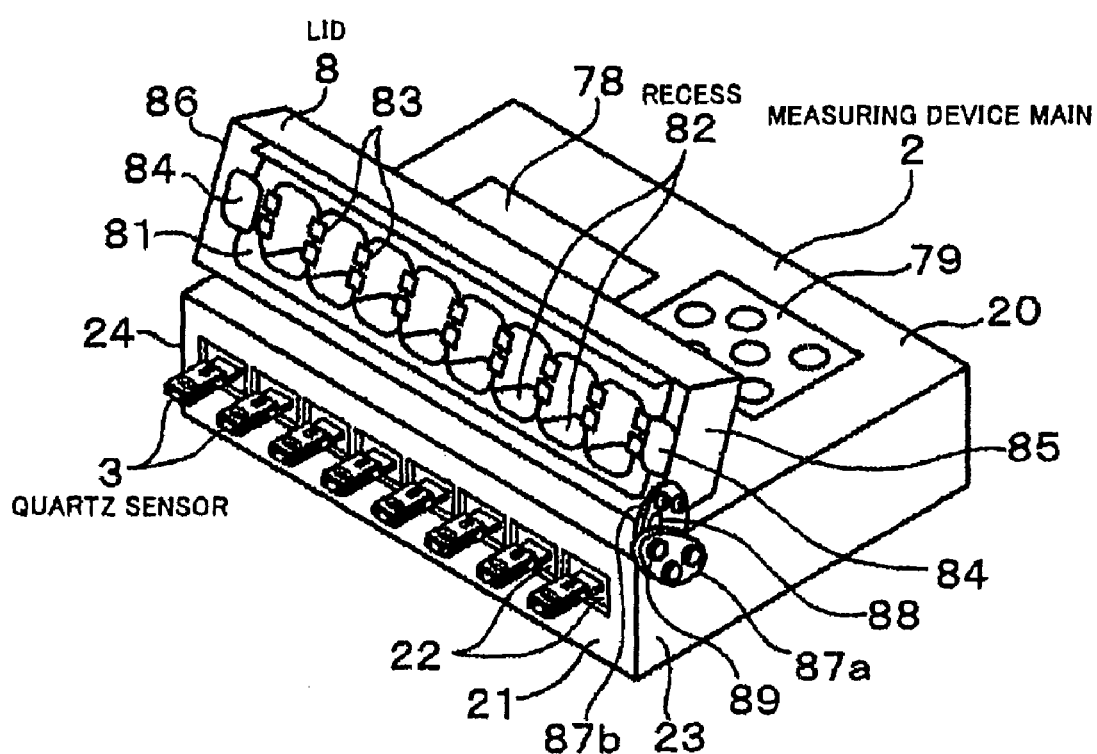
FIG. 1 is a perspective view showing an appearance of an embodiment of a component measuring device relating to the present invention in which a lid is opened.

An embodiment of a component measuring device relating to the present invention will be explained using the drawings. FIG. 1 is a perspective view showing a total structure of the component measuring device relating to the present invention. The measuring device is structured such that a plurality (for instance, 8 pieces) of quartz sensors 3 are able to be detachably installed to a side 21 of a measuring device main unit 2.

Figure 2:
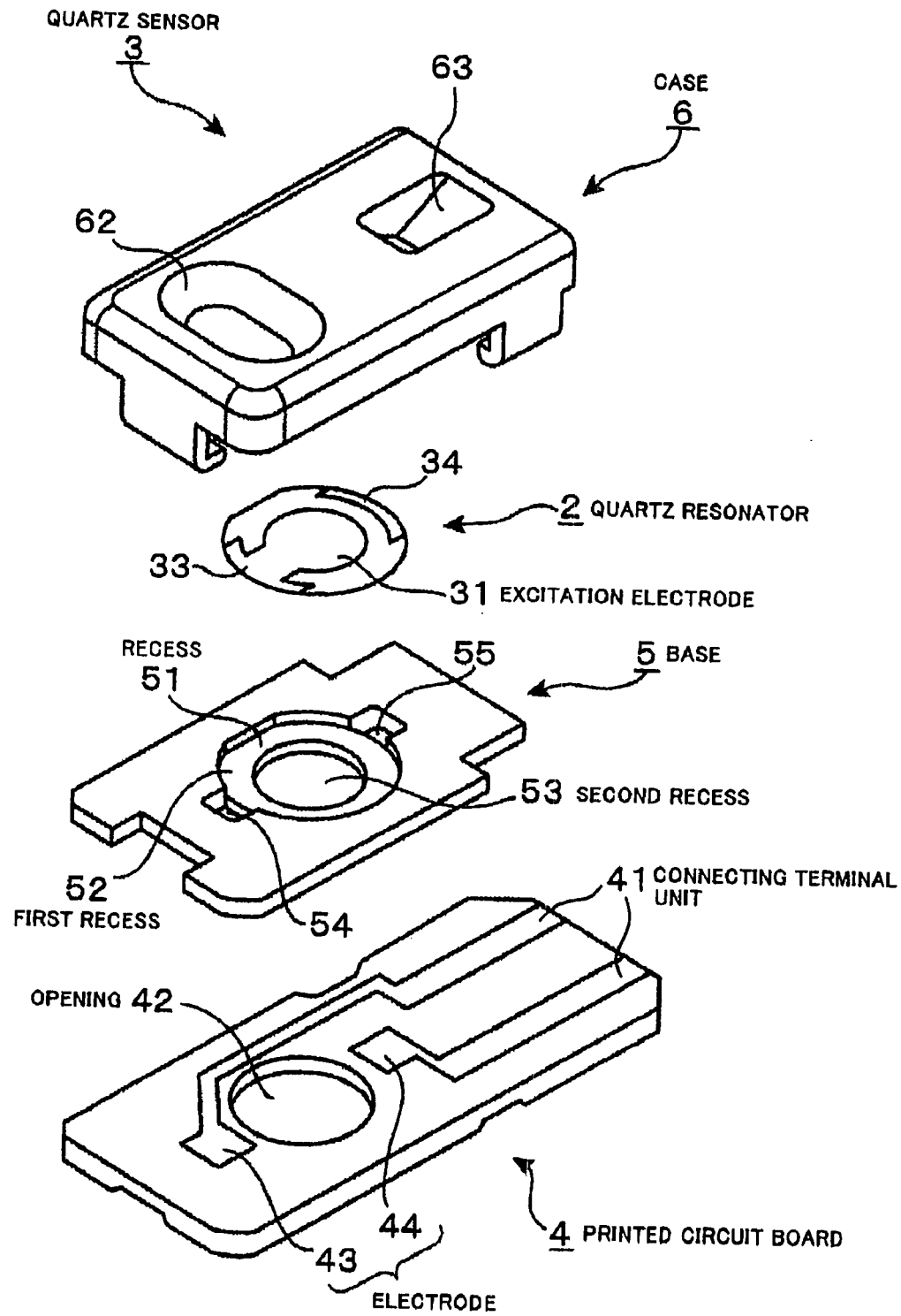
FIG. 2 is an exploded perspective view showing an example of a quartz sensor used in the measuring device.

The quartz sensor 3 will be explained first using FIGS. 2 to 4. The quartz sensor 3 is a Langevin type quartz sensor, and a base 5 serving as a quartz holding member is mounted on a printed circuit board 4 which serves as a wiring circuit as shown in FIG. 2. A quartz resonator 30 is housed in a housing area formed in the base 5, and a case 6 is fixed to the printed circuit board 4 so as to cover the quartz resonator 30 and the base 5 from above. In this embodiment, a holding unit is composed of the printed circuit board 4 and the base 5 serving as the quartz holding member.

The respective units will be explained next. 30 in the drawing is a round quartz resonator having an equivalent thickness of 1 μm to 300 μm, preferably 185 μm, and 31, 32 are round foil-shaped excitation electrodes having a diameter smaller than the quartz resonator 30, and stuck on both surface sides of the quartz resonator 30 respectively. Foil-shaped derivation electrodes 33 and 34 are respectively connected to these excitation electrodes 31 and 32. These derivation electrodes 33 and 34 are pulled out a little toward the outside of the excitation electrodes 31 and 32 in a band-like form, bent along the end surface of the quartz resonator 30 in a state to expand arcuately along the periphery of the quartz resonator 30, and bent around toward the other side of the quartz resonator 30 so as to form as a shape arcuately expanding along the periphery of the other surface.

The printed circuit board 4 is formed in a rectangular sheet, attached to and detached from the measuring device main unit 2, is provided with a connecting terminal unit 41 electrically connected to a circuit in the measuring main unit 2 and a hole 42. Thin shout electrodes 43 and 44 of which one end sides are connected to the derivation electrodes 33 and 34 of the quartz resonator 30, and the other end sides extend toward the connecting terminal unit 41 are stuck on the one end side of the printed circuit board 4. The equivalent thickness of the excitation electrodes 31, 32, the derivation electrodes 33, 34 and the electrodes 43, 44 are about 0.2 μm. Although gold or silver is suitable for a material for these electrodes, gold is especially preferable because of high frequency stability in a fluid, and resistance to oxidation of electrode surface under preservation in the air before use.

The base 5 is made of an elastic material such as rubber, a housing area for the quartz resonator 30 and a round recess 51 forming the airtight space are formed on one surface side. The recess 51 is formed in two tiers, and a first recess 52 on the first tier is for forming the above-described housing area, and formed in a ring shape to serve as a portion for placing the backside peripheral area of the quartz resonator 30. The quartz resonator 30 is placed in the first recess 52 so that the position is restrained by an inner wall of the first recess 52.

A second recess 53 on the second tier is formed with a round shape at a position lower than the first recess 42 with the intention that this will form the airtight space with an outer diameter greater than that of the excitation electrode 32 on the other surface side of the quartz resonator 30 and smaller than that of the quartz resonator 30. The back surface side of the second recess 53 is fitted into the hole 42 of the printed circuit board 4 thereby fixing the base 5 to the printed circuit board 4. Holes 54 and 55 are formed on the outside of the first recess 52 in the base 5, so as to be in contact with the derivation electrodes 33 and 34 when the quartz resonator 30 is housed in the base 5.

The quartz resonator 30 is placed on the upper surface of the first recess 52 so as to cover the second recess 53. The position thereof is fixed in a state that it is restrained by the inner wall of the first recess 52 by elastic restoration force of the base 5, thereby an airtight space is formed by the second recess 53 on the other surface side of the quartz resonator 30. The quartz resonator 30, the base 5 and the printed circuit board 4 are closely fixed by filling a conductive adhesive 56, for instance, an adhesive which is a mixture of an epoxy based adhesive and a silver paste into the holes 54 and 55. The periphery of the first recess 52 and the periphery on the back surface side of the quartz resonator 30 are also closely fixed with the conductive adhesive. Through this process, the electrodes 43, 44 formed on one surface side of the printed circuit board and the derivation electrodes 33, 34 of the quartz resonator 30 are electrically connected via the conductive connector 56.

As described above, when the position of the quartz resonator 30 is restrained by the inner wall of the first recess 52, and the quartz resonator 30 is positioned within the first recess 52, the excitation electrode 32 on the other surface side is provided at the position facing to the space formed by the second recess 53. Since the quartz resonator 30 is closely fixed to the periphery of the first recess 52 by an adhesive as described previously, the space in the second recess 53 is an airtight space, so that the excitation electrode 32 on the other surface side is in contact with the airtight space within the second recess 53. An adsorbing layer which adsorbs the target component consisting of, for instance, an antibody, is formed on the front surface of the excitation electrode 31 on one surface side of the quartz resonator 30.

The printed circuit board 4 on which the quartz resonator 30 and the base 5 are installed is structured so as to be covered with a plastic case 6 from the upper side of the quartz resonator 30. The case 6 is structured so as to cover in and around the area where the quartz resonator 30 of the printed circuit board 4, the one end side which is a connecting terminal unit 41 of the print circuit board 4 is exposed toward outside of the case 6, so that the connecting terminal unit 41 is attached to and detached from the measuring device main unit 2.

Figure 3:
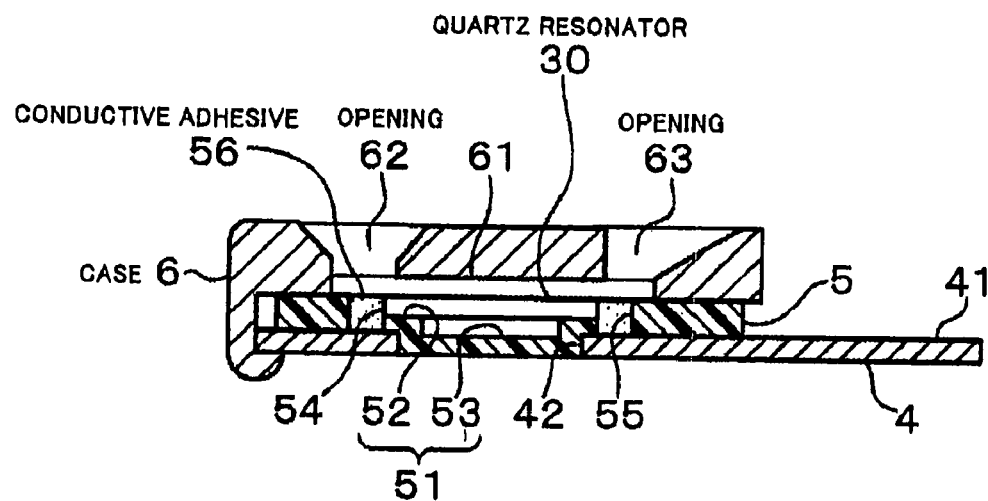
FIG. 3 is a cross section showing an example of the quartz sensor.
Figure 4:
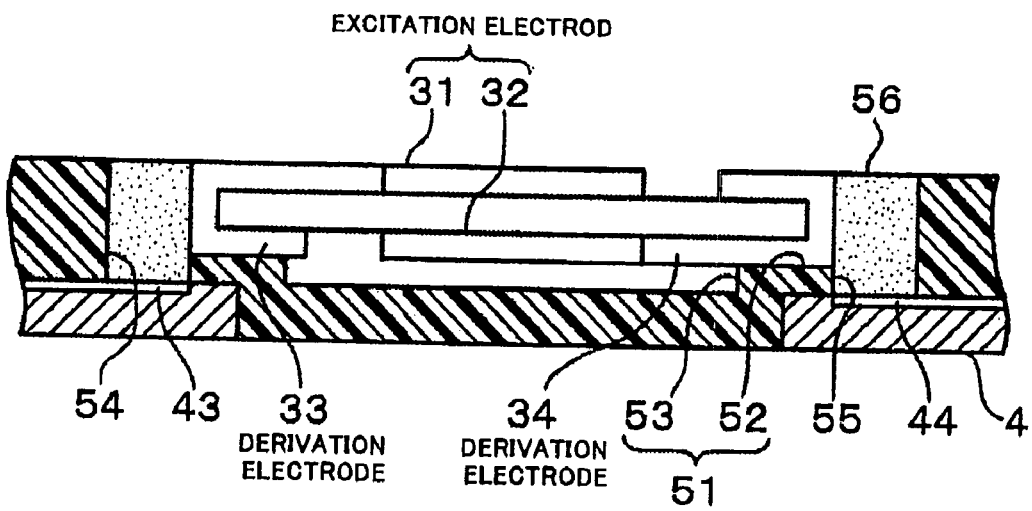
FIG. 4 is a cross section showing an example of the quartz sensor.
Figure 5:
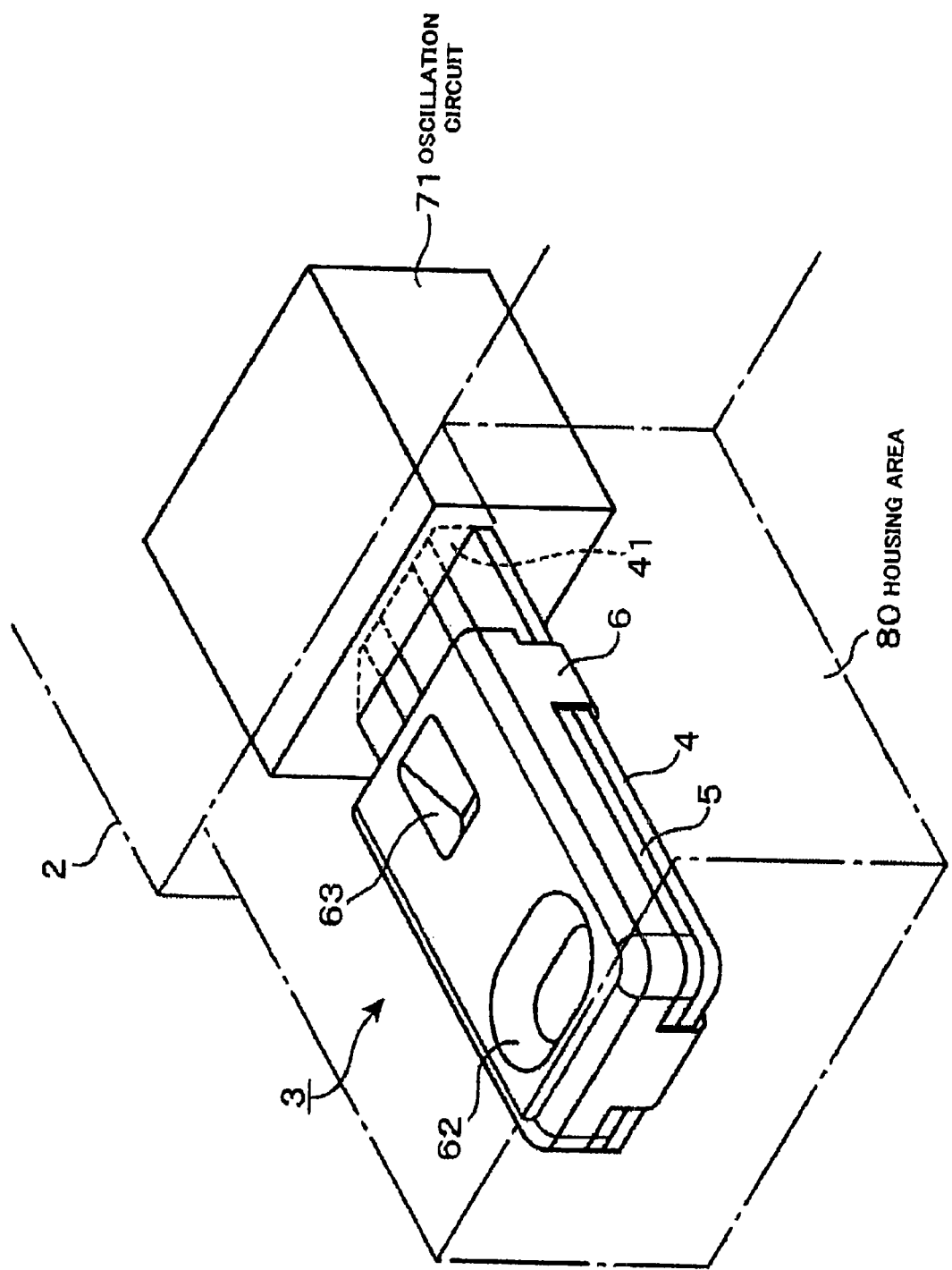
FIG. 5 is perspective view showing an example of the quartz sensor.

The case 6 is provided so as to form a plane 61 nearly the same as or wider than the quartz resonator 30 on the upper surface side of the quartz resonator 30 as shown in FIG. 3, and two openings 62 and 63 are formed for supplying the sample solution to the plane 61.

The measuring device main unit 2 will be explained using FIG. 1 and FIGS. 5 to 8. The measuring device main unit 2 is placed on a mounting plane of, for instance, a work bench or the like, and is provided with a conductive outer box 20 formed nearly in a rectangular shape. On one side of the outer box 20, a plurality (for instance, 8 pieces) of the quartz sensors 3 are detachably provided, for instance, in a line. Specifically, in the inside of the measuring device main unit 2, a plurality of (8 pieces in this embodiment) oscillation circuits 71 corresponding to the quartz sensor 3 along one side of the measuring device main unit 2 is horizontally arranged in a line. The oscillation circuit 71 is a means for oscillating the quartz resonator 30 of the quartz sensor 3. On the conductive side 21 forming the side surface of the measuring device main unit 2, 8 pieces of openings 22 are formed on the positions corresponding to the oscillation circuits 71, so that the connecting terminal unit 41 of the printed circuit board is installed in a state to be plugged to the corresponding oscillation circuits 71 through these openings 22. In this embodiment, a portion in the oscillation circuit 71, to which the connecting terminal unit 41 of the printed circuit board 4 is installed forms a connecting terminal unit, and the connecting terminal unit 41 of the printed circuit board 4 is installed to the connecting terminal unit of the oscillation circuit 71 in a state that the quartz sensor 3 is suspended in the air above the mounting plane.

Figure 6:
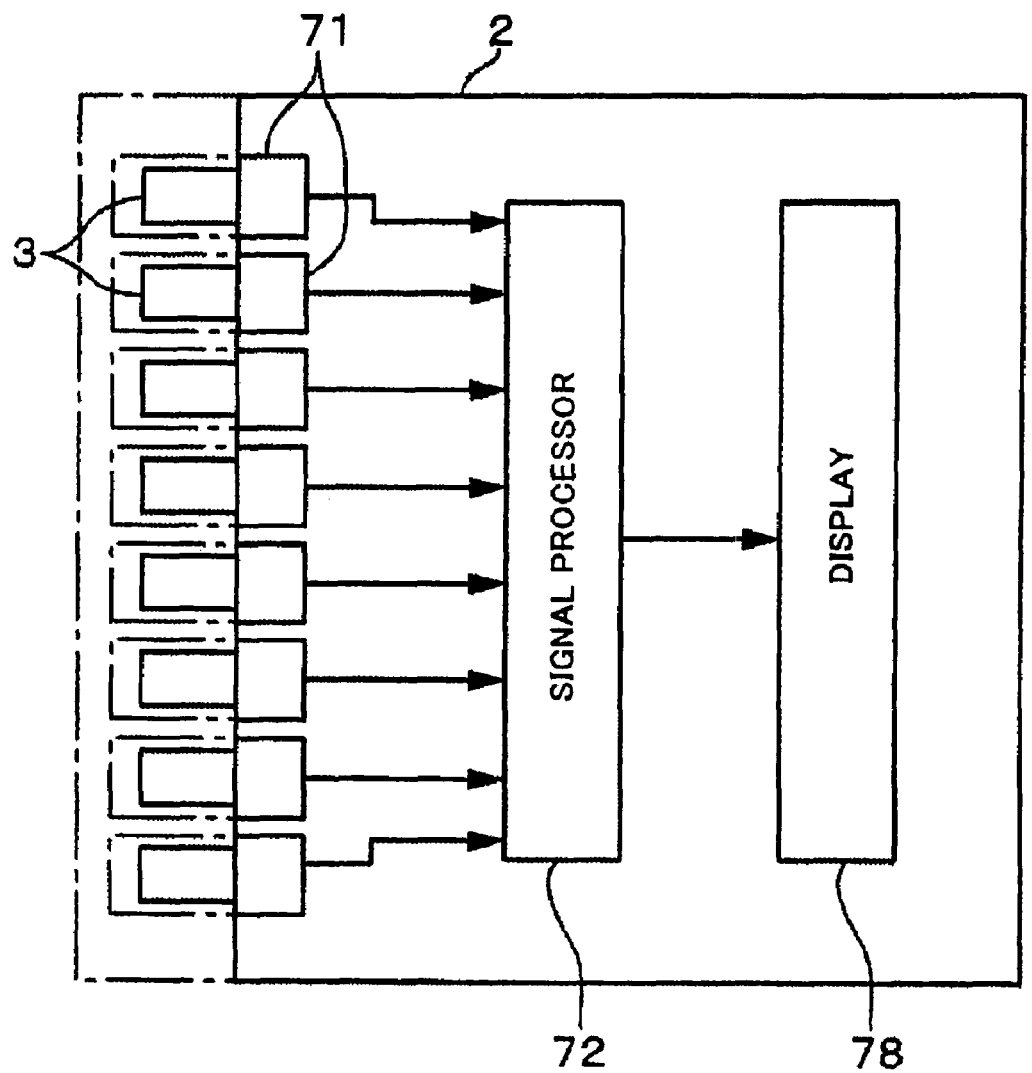
FIG. 6 is a block diagram showing the quartz sensors connected to the measuring device and an example of the inside structure of the measuring device main unit.
Figure 7:
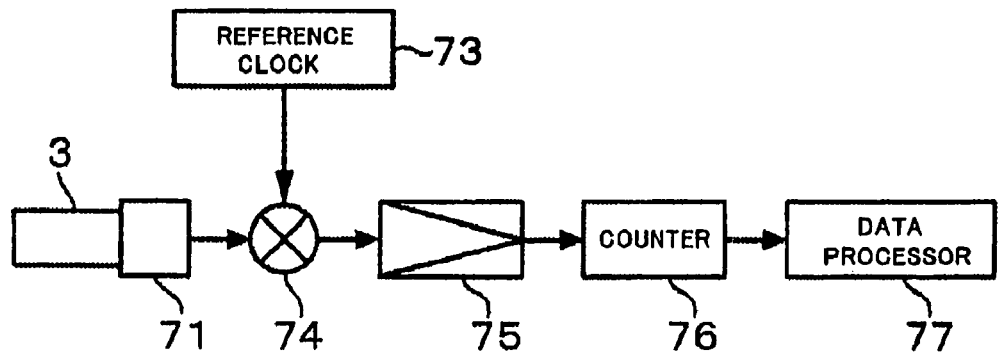
FIG. 7 is a block diagram showing an example of a specific structure of a signal processor.

These oscillation circuits 71 are designed to be electrically connected to the electrodes 42 and 43 via the connecting terminal units 41 of the printed circuit boards 4 when the printed circuit boards are installed, and are connected to a signal processor 72 respectively as shown in a block diagram showing an embodiment of the measuring device in FIGS. 6 and 7. The signal processor 72 includes a reference clock generator 73 generating a reference frequency signal connected to the oscillation circuit 71, a frequency difference detector 74 composed of, for instance, a heterodyne detector for taking out a frequency signal corresponding to a difference between both based on the frequency signal from the oscillation circuit 71 and the clock signal from the reference clock generator 73, an amplifier 75, a counter 76 for counting the frequency of an output signal from the amplifier 75, and a data processor 77, so that the concentration of a target component determined in the data processor 77 is displayed on a display 78.

Note that a channel switchover unit (not shown) is provided between the oscillation circuit 71 and the frequency difference detector 74, so that the respective outputs (8 channels) from 8 pieces of the oscillation circuits 71 are switched over in sequence to be connected to the frequency difference detector 74 in sequence. 79 in FIG. 1 is a control panel. It is also adoptable that the threshold value for variations of the frequency is established in advance to determine the presence of dioxin instead of displaying the dioxin concentration on the display 78.

As the frequency of each quartz sensor 3, for instance, 9 MHz is selected, and as the frequency of the reference clock generator 73, for instance, 10 MHz is selected. Although when, for instance, dioxin which is an object to be measured is not adsorbed on the quartz resonator 30, the frequency difference detector 74 outputs the frequency signal (frequency difference_signal) of 1 MHz which is a difference between the frequency from the quartz sensor 3 side and the frequency of the reference clock, when dioxin is adsorbed on the quartz resonator 30, the natural frequency varies, which varies_the frequency difference signal, so that the count value on the counter 76 varies. Note that a computer may be connected to the measuring device main unit 2 and a data processor may be provided in the computer. The display may be provided separately from the measuring device main unit 2.

The measuring device main unit 2 has a lid 8 covering the respective quartz sensors 3 which are installed to the measuring device main unit 2. The lid 8 is formed in a long and narrow rectangular box shape as shown in FIG. 1, and has a conductive wall 81 which abuts on the side 21 when closed. Recesses 82 to form independent areas 80 for housing a plurality of quartz sensors 3 are formed in the wall 82 so that the quartz sensors 3 are shielded from each other when they are installed. The number of the recesses 82 which form the housing areas 80 exactly equals the number of sensors 3, that is 8 in this embodiment.

The recess 82 is affixed with, for instance, a metal foil on the inner wall thereof, the inner wall is formed with a conductive material, and the area covered with the lid 8 is designed to be shielded. When the lid 8 is closed, the wall 81 surrounding the recess 82 covers the surroundings of the opening 22 in which the quartz sensor 3 is installed, so as to be housed in a state that each quartz sensor 3 is separated from each other by a partition. Thus, the housing area 80 for the quartz sensor 3 is formed, which is enclosed and electrically shielded by the sides 21 around the opening 22 of the measuring device main unit 2, the recess 82 of the lid 8, and the wall 81 around the recess 82.

A spring 83 formed of a conductive material is included between the recesses 82 adjacent to each other at a position to be in contact with the sides 21 between the openings 22 of the measuring device main unit 2, which are adjacent to each other, when the lid 8 is closed. When the lid 8 is closed, the spring 8 abuts on the side 21 of the measuring device main unit 2, so that the impact at the time of closing the lid 8 is relaxed. The conductive outer box, the recess 82 and the lid 81 are electrically connected, so that an electromagnetic shield is formed by connecting to the earth. The spring 83 is a conductive metal spring made of, for instance, a copper titanium alloy, and is preferably formed of material excellent in conductivity. It is connected to the earth via the spring 83 and the conductive outer box 20. A shock absorbing material 84, for instance sponge, for absorbing an impact caused by closing of the lid 8 is installed on the lid 8, for instance, outside of two outermost recesses 82.

Figure 8:
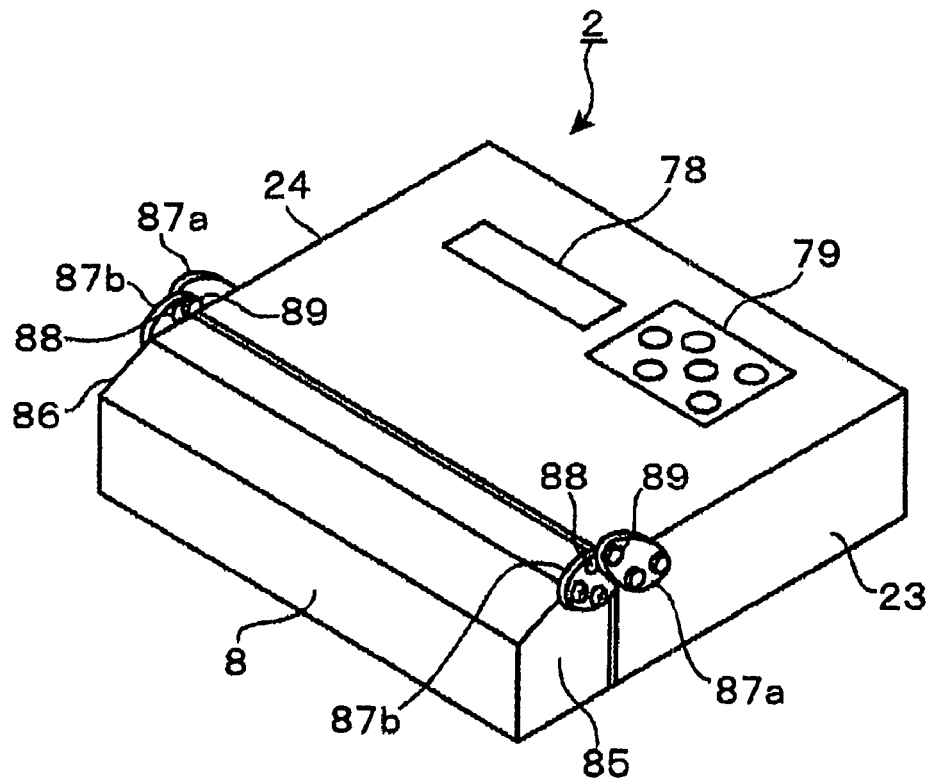
FIG. 8 is a perspective view showing an appearance of the above-described measuring device in which the lid is closed.

Such a lid 8 is rotatably provided around the shaft horizontally extending along the side of the measuring device main unit 2. A side wall 23 (24) of the measuring device main unit 2 is connected to a wall 85 (86) on both sides of the lid 8 via a pivot mechanism. The pivot mechanism includes a first plate 87a screwed to the side wall 23 (24) and a second plate 87b screwed to the wall 85 (86). A connecting shaft 89 is formed on the first plate 87a and a guide groove 88 is formed on the second plate 87b, and the wall 85 (86) can pivot around the horizontal axis by the connecting shaft 89 guided by the guide groove. Accordingly, it can be opened and closed between a state of the lid 8 in open (the position at which the quartz sensor is exposed as shown in FIG. 1) and a state of the lid 8 in close (the position at which the quartz sensor is covered as shown in FIG. 8). In this embodiment, the connecting shaft 89 corresponds to a shaft horizontally extending along the side of the measuring device main unit 2.

In such a component measuring device, first a plurality (8 pieces, for instance) of the quartz sensors 3 is prepared, and an antibody which is an adsorbing layer for selectively adsorbing an object to be measured, for instance, dioxin is stuck on one surface side of the quartz resonator 30 (for instance, on the excitation electrode 31). These 8 pieces of the quartz sensors 3 are installed on the measuring device main unit 2 by inserting the connecting terminal unit 41 of the printed circuit board 4 into the connecting terminal unit of the oscillation circuit 71 of the measuring device main unit 2.

Then, as a blank solution as described before, pure water is dropped (liquid pouring) from the openings 62 and 63 into each quartz sensor 3, and the frequency at this time counted by the counter 76 is stored in a storing unit of a data processing unit 57. More in detail, for instance, pure water as a sample is poured into each quartz sensor 3, and the frequency counted at this time with the counter 76 is stored as the blank into a storing unit of the data processing unit 77.

Then, 8 kinds of sample solutions different in dilution ratio of the target component from each other are prepared, and the concentration of these sample solutions are measured by each quartz sensor 3. In other words, the sample solution is poured from the openings 62 and 63, the frequency at this time is counted with the counter 76, and the variation (variation in the natural frequency of the quartz resonator) between the frequency of the pure water poured into each quartz sensor 3 and the frequency of dioxin so that the concentration of dioxin in each sample solution is calculated from the first calibration curve prepared in advance. Thus, for instance, the frequency difference which is variation between, for instance, the frequency of the pure water and that of dioxin at this time, and the concentration of dioxin of each sample solution are displayed on the display 78.

Figure 9:
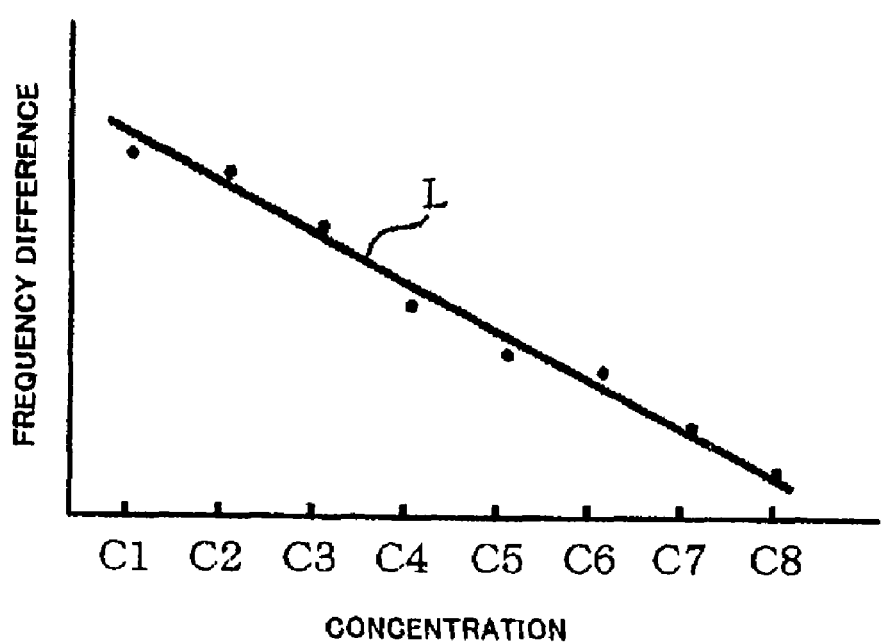
FIG. 9 is a characteristic diagram showing relation the frequency difference and the concentration of the measuring target component in the sample solution different in dilution ratio when the concentration of the target component is measured using a plurality of quartz sensors.

Then, for instance, an operator plots the frequency difference and the concentration of dioxin of each sample solution (C1 to C8), and the second calibration curve as shown in FIG. 9 is drawn so that the variations of dioxin concentration of each sample solution is made minimum The concentration of dioxin in the sample solution is determined based on the second calibration curve. When this concentration is determined, the concentration in the sample solution before dilution can be obtained from the dilution ratio of a sample solution in the quartz sensor 3 corresponding to the concentration.

The reason for performing the following process of preparing a plurality types of sample solution different in dilution ratio, and measuring the concentrations of respective sample solutions using a plurality of quartz sensors 3 to determine the concentrations of the sample solutions based on the measured values is as follows. That is, the frequency of the quartz sensor 3 sometimes deviates though slight due to variation in the manufacturing process. When the measurement is conducted using only one sensor, the variation of the frequency of the quartz sensor reflects the concentration measurement, which can result in greater errors in measurement. The reason of performing the measurement in the manner described above is to restrain the error.

A measuring device using the quartz sensor 3 like this is detachably provided with a plurality of Langevin type quartz sensors 3 on the side of the measuring device main unit 2 so that the adsorbing layer thereof faces upward.

Therefore it is possible to easily perform the concentration measurement of the sample solution by installing the quartz sensor 3 in the oscillation circuit 71 provided in the measuring device main unit 2 and dropping the sample solution on one surface side of the quartz resonator 30 from the openings 62 and 63.

Accordingly, when a plurality (for instance 8 pieces) of quartz sensors 3, it is possible to conduct the measuring work in a lump by, for instance, switching over channels in turn. Therefore, it is possible to conduct the measurement work easier compared with the case of measuring samples repeatedly using one quartz sensor, which makes it possible to drastically reduce the time required for measuring work.

Furthermore, compared with the conventional case of conducting measurement by immersing the quartz sensor into the sample solution on a work bench, it does not require a troublesome work of adding a sample to the quartz sensor 3 at some other spot and carrying it to the measuring unit. In addition, there is no possibility of bringing a vessel containing the sample solution down, and it is possible to perform the measuring work easily and promptly.

Furthermore, since the quartz sensor the measuring device main unit 2 is installed in a suspended state from the mounting place on which the measuring device main unit 2 is placed, there is no wiring routed around on the work bench for connecting the quartz sensor and the measuring device main unit. Therefore, there is no possibility of bringing the quartz sensor down by getting the wiring snagged on. Still further, since it is possible to perform a concentration measuring work of a plurality of samples in parallel using a plurality of quartz sensor 3, the time required for the measuring work can be drastically reduced compared with the case of using one quartz sensor and measuring repeatedly.

At this time, since the printed circuit board 4 is provided with the quartz resonator 30 via the base 5 in the above embodiment, and connection with the measuring device main unit 2 can be performed by inserting or removing the connecting terminal unit 41 of the above printed circuit 4 into or from the connecting terminal unit of the oscillation circuit 71 in the measuring device main unit 2, attaching, detaching and electric connection can be easily conducted.

Furthermore, in the above embodiment, since the surrounding of the quartz sensor 3 is covered with the conductive lid 8 after installing the quartz sensor 3, the quartz sensor 3 is blocked from dust from the atmosphere in which the measuring device main unit 2 is placed, from electromagnetic waves coming from portable phones or microwave ovens, from disturbance such as a current of air, human body temperature, or the like, these bad influences can be removed, so that the measurement with higher accuracy can be conducted. Furthermore, the quartz sensor 3 is provided inside the conductive housing area extending over between the measuring device main unit 2 and the lid 8, and each housing area 80 is divided in an independent state from each other so as to be electrically shielded from outside. Therefore, electromagnetic waves coming from outside such as portable phones or microwave ovens are blocked and these bad influences are removed.

Each quartz sensor 3 is set at the same frequency, it is extremely difficult to set at the same frequency due to fluctuation during manufacturing. Therefore, the frequency of adjacent quartz sensors 3 show a slight deviation though they are very close. Accordingly, it is possible to restrain the interference between frequencies of the adjacent quartz sensors 3 to conduct accurate measurement for every quartz sensor 3 by shielding the surrounding of the quartz sensor 3 individually.

Figure 10:
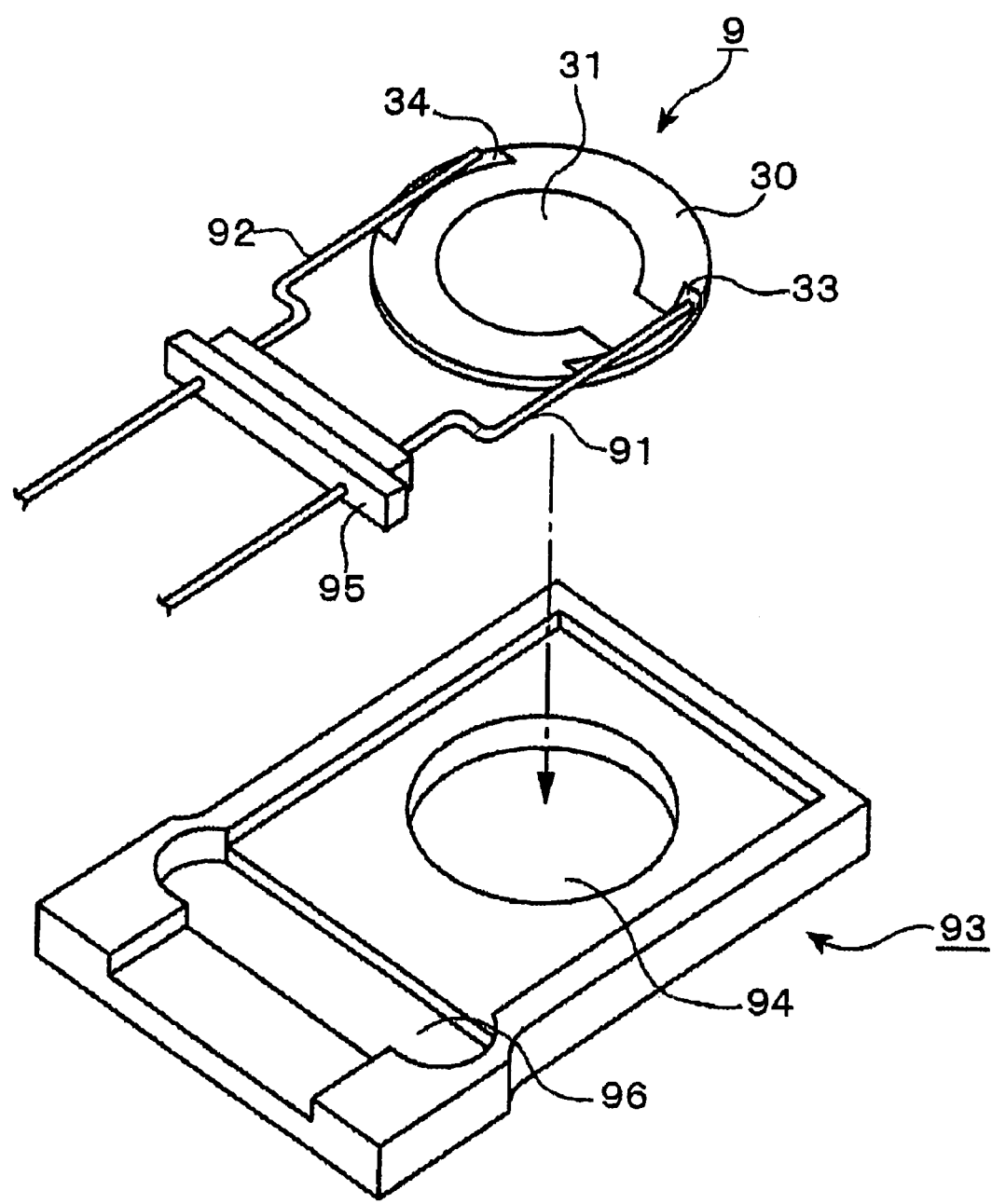
FIG. 10 is an exploded perspective view showing an example of other quartz sensors.

In the present invention described above, it is possible to use a quartz sensor 9 having a structure shown in FIG. 10. The quartz sensor 9 of this structure includes excitation electrodes 31, 32, and derivation electrodes 33, 34 on both surfaces of the quartz resonator 30 similarly to the above-described quartz sensor. The difference in structure between the present structure and that described above is that the electric connection with a circuit in the measuring device main unit 2 is not conducted via the connecting terminal unit 41 of the printed circuit board 4, but via a pair of supporting line members 91 and 92 connected to the derivation electrodes 33 and 34 at the one end thereof. These supporting line members 91 and 92 are composed of a piano wire and the other sides of the supporting line members 91 and 92 are connected to the oscillation circuit 71 of the measuring device main unit 2.

93 in the drawing is a base made of plastic, is surrounded by frames on three sides and a housing area for the quartz resonator 30 is formed. A round recess 94 is formed in the housing area. When the quartz resonator 30 is housed in the housing area, an airtight space where the excitation electrode 32 on the other surface side of the quartz resonator 30 comes in contact with is formed. 95 in the drawing designates a holder for the supporting line members and 96 designates a receptacle defining the position of the holder.

In such a quartz sensor 9, by attaching or detaching the tips of the supporting members 91 and 92 to or from the connecting terminal unit of the oscillation circuit 71 of the measuring device main unit 2, the quartz sensor 9 is detachably installed in the measuring device main unit 2. Since a plurality of quartz sensors 9 is detachably installed also in this component measuring device, it is possible to perform the measuring work for the concentration of a target component using a plurality of quartz sensors 9 easily and in a short time similarly to the above embodiment.

A lid may be provided so as to enclose the surrounding of the quartz sensor 9 installed in the measuring device main unit 2, or a plurality of quartz sensors 9 may be housed in housing areas different from each other in an electrically independent state, similarly to the above-described embodiment.

Figure 11:
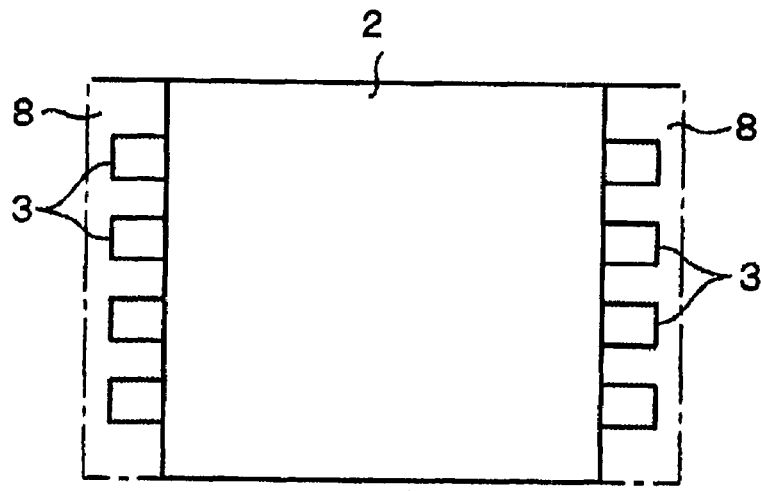
FIG. 11 is a plan view showing a structural example of another measuring device according to the present invention.

In the above-described present embodiment, the number of the quartz sensors 3 detachably installed in the measuring device main unit 2 is sufficient if it is two or more, and is not necessarily limited to 8. It is possible to provide one or more quartz sensors 3 on two or more side surfaces as shown in FIG. 11, instead of providing all of the plural quartz sensors 3 in one side surface of the measuring device main unit 2. In addition, when a plurality of quartz sensors 3 is prepared, it is not always necessary to use all of them at the time of measuring the target component to be measured.

Figure 12:
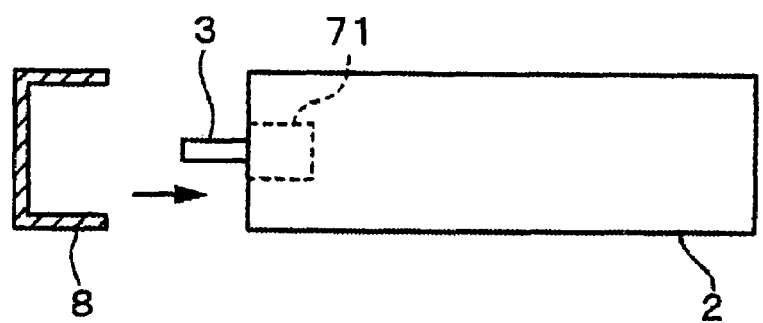
FIG. 12 is a plan view showing a structural example of still another μmeasuring device according to the present invention.
Figure 13:
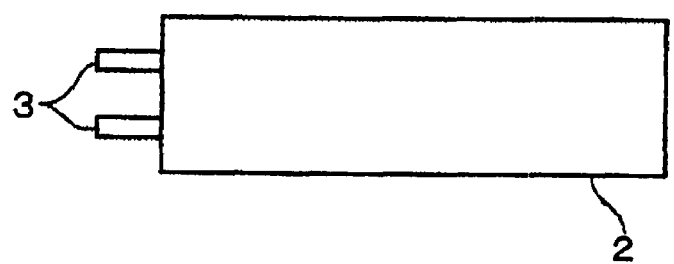
FIG. 13 is a side view showing a structural example of yet another measuring device according to the present invention.
Figure 14:
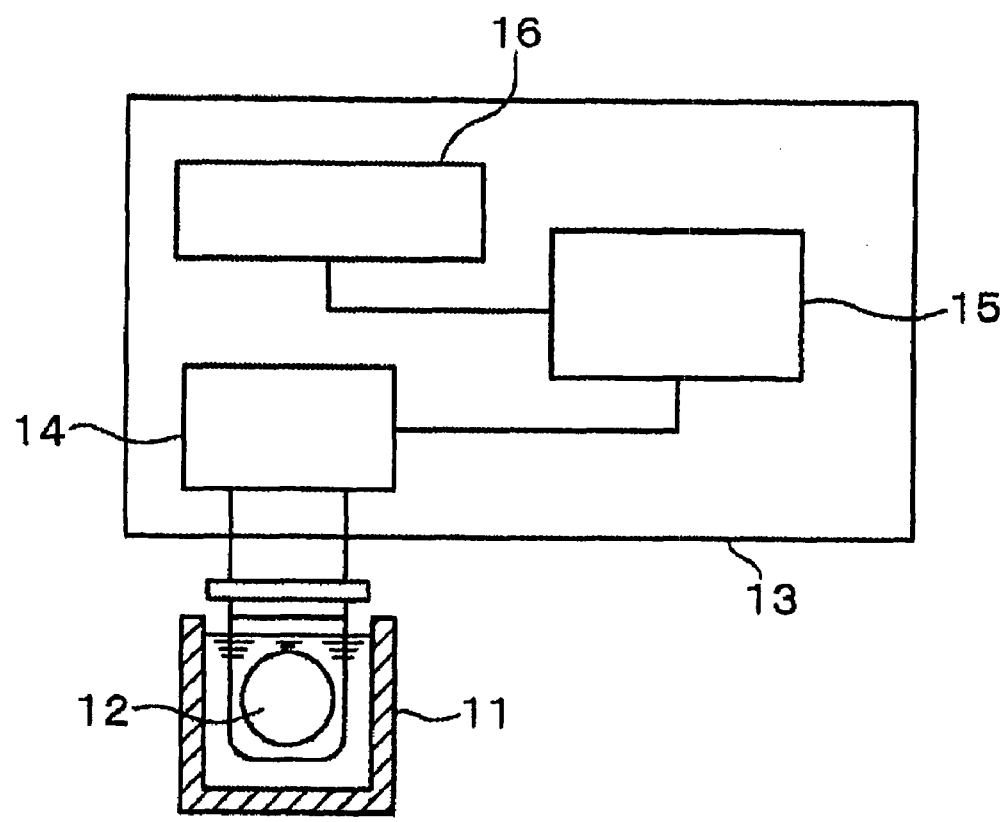
FIG. 14 is a block diagram showing the structure of a conventional component measuring device.

Furthermore, the lid 8 is arranged independently from the measuring device main unit 2, and a plurality of quartz sensors 3 is installed in the measuring device main unit 2 and the lid 8 may be equipped after a sample solution is poured as shown in FIG. 12. In addition, a plurality of recesses 82 is formed in the lid 8, it is possible to cover the respective quartz sensors 3 in a room with the cover 8, instead of covering each quartz sensor independently. Moreover, as for a plurality of the quartz sensors 3, two or more quartz sensors 3 may be vertically arranged on the side surface of the measuring device main unit 2 in a state that the excitation electrode 31 is in contact with the sample solution on one surface side thereof.

The invention claimed is:

1. A measuring device for detecting a target component in a sample solution, comprising:
   at least one sensor unit configured as a sensor including:
      a substrate having first and second ends on opposite ends, and substrate surface with a printed circuit formed thereon, said printed circuit including first and second terminal contacts and first and second conductors, said first and second terminal contacts being disposed at said first end and respectively connected to said first and second conductors;
      a resonator having first and second excitation electrodes on respective first and second opposing sides, said first excitation electrode having an adsorbing layer disposed thereon which adsorbs said target component, said resonator having first and second lead electrodes respectively electrically connected to said first and second excitation electrodes;

said resonator being supported over and parallel to said substrate proximate said second end with said second excitation electrode suspended facing said substrate and parallel to said substrate surface, and said second excitation electrode suspended over a sealed space defined at least in part by said resonator and said substrate;

said first and second conductors being respectively electrically connected to said first and second lead electrodes of said resonator by a conductive adhesive, said second lead electrode being disposed arcuately about a portion of a perimeter of said seal space and a seal being effect to said second lead electrode; and a case having a first opening surrounding said first excitation electrode and configured to define a sample solution accommodation area communicating with said adsorbing layer, said case having a second opening configured for injection of said sample solution and communicating with said sample solution accommodation area;

a measuring device having a device body and including an oscillation circuit therein;

said measuring device defining insertion holes arranged in a horizontal line and each configured to detachably accept one of said at least one sensor unit, each of said insertion holes having contacts for connecting the first and second terminal contacts to the oscillation circuit; and said measuring device being configured to determine, based on oscillation of said at least one resonator, at least one of:

presence/absence of the target component; or a concentration of the target component in the sample solution.

2. The component measuring device of claim 1, wherein said substrate includes a substrate recessed portion opposing said second excitation electrode to define said sealed space, and said substrate recessed portion being larger than said second excitation electrode.

3. The component measuring device of claim 1, further comprising a lid movably mounted to said measuring device and configured to move from a first position covering said at least one sensor unit disposed in one of said insertion holes and shielding said at least one sensor unit from an outside environment in conjunction with said device body, and a second position exposing said at least one sensor unit to said outside environment.

4. The component measuring device of claim 3, wherein the insertion holes are provided on a lateral surface of the device body, and the lid is configured to cover an upper surface, side surface and a lower surface of said at least one sensor unit.

5. The component measuring device of claim 4, wherein said lid is movably mounted to said measuring device so as to rotate about a horizontal axis between said first and second positions, said at least one sensor unit is a plurality of sensor units configured as is said sensor and said lid is configured to cover said plurality of sensor units when in said first position, and to expose said sensor units such that said sensor units are exposed in a vertical direction to accept unobstructed pouring of said sample solution thereon.

6. The component measuring device of claim 5, wherein said lid is configured to provide divided areas wherein individual ones of said sensor units are independently shielded from each other.

7. The component measuring device of claim 3, wherein said lid is configured to provide divided areas wherein individual ones of said sensor units are independently shielded from each other.

8. The component measuring device of claim 7, further comprising an elastic member disposed between said resonator and said substrate, said elastic member defining an elastic member aperture for communicating said second excitation electrode to said substrate and forming a seal between said resonator and said substrate to seal said scaled space.

9. The component measuring device of claim 8, wherein said elastic member includes first and second through holes through which said conductive adhesive connects said first and second conductors respectively to said first and second lead electrodes.

10. The component measuring device of claim 9, wherein said elastic member aperture includes a elastic member recess having an annular recess bottom upon which said resonator seats and said first and second through holes being communicated to said elastic member recess at locations of said first and second lead electrodes.

11. The component measuring device of claim 6, further comprising an elastic member disposed between said resonator and said substrate, said elastic member defining an elastic member aperture for communicating said second excitation electrode to said substrate and forming a seal between said resonator and said substrate to seal said sealed space.

12. The component measuring device of claim 11, wherein said elastic member includes first and second through holes through which said conductive adhesive connects said first and second conductors respectively to said first and second lead electrodes.

13. The component measuring device of claim 12, wherein said elastic member aperture includes a elastic member recess having an annular recess bottom upon which said resonator seats and said first and second through holes being communicated to said elastic member recess at locations of said first and second lead electrodes.

14. The component measuring device of claim 2, further comprising an elastic member disposed between said resonator and said substrate, said elastic member defining an elastic member aperture for communicating said second excitation electrode to said substrate and forming a seal between said resonator and said substrate to seal said sealed space.

15. The component measuring device of claim 14, wherein said elastic member includes first and second through holes through which said conductive adhesive connects said first and second conductors respectively to said first and second lead electrodes.

16. The component measuring device of claim 15, wherein said elastic member aperture includes a elastic member recess having an annular recess bottom upon which said resonator seats and said first and second through holes being communicated to said elastic member recess at locations of said first and second lead electrodes.

17. A measuring device for detecting a target component in a sample solution, comprising:

at least one sensor unit configured as a sensor including:

a substrate having first and second ends on opposite ends, and substrate surface with a printed circuit formed thereon, said printed circuit including first and second terminal contacts and first and second conductors, said first and second terminal contacts being disposed at said first end and respectively connected to said first and second conductors;

a resonator having first and second excitation electrodes on respective first and second opposing sides, said first excitation electrode having an adsorbing layer disposed thereon which adsorbs said target component, said resonator having first and second lead electrodes respectively electrically connected to said first and second excitation electrodes;

said resonator being supported over and parallel to said substrate proximate said second end with said second excitation electrode suspended facing said substrate and parallel to said substrate surface, and said second excitation electrode suspended over a sealed space defined at least in part by said resonator and said substrate;

said first and second conductors being respectively electrically connected to said first and second lead electrodes of said resonator by a conductive adhesive; and a case having a first opening surrounding said first excitation electrode and configured to define a sample solution accommodation area communicating with said adsorbing layer, said case having a second opening configured for injection of said sample solution and communicating with said sample solution accommodation area; and an elastic member disposed between said resonator and said substrate, said elastic member defining an elastic member aperture for communicating said second excitation electrode to said substrate and forming a seal between said resonator and said substrate to seal said sealed space, a measuring device having a device body and including an oscillation circuit therein;

said measuring device defining insertion holes arranged in a horizontal line and each configured to detachably accept one of said at least one sensor unit, each of said insertion holes having contacts for connecting the first and second terminal contacts to the oscillation circuit; and said measuring device being configured to determine, based on oscillation of said at least one resonator, at least one of:
 presence/absence of the target component; or
 a concentration of the target component in the sample solution.

18. The component measuring device of claim 17, wherein said elastic member includes first and second through holes through which said conductive adhesive connects said first and second conductors respectively to said first and second lead electrodes.

19. The component measuring device of claim 18, wherein said elastic member aperture includes a elastic member recess having an annular recess bottom upon which said resonator seats and said first and second through holes being communicated to said elastic member recess at locations of said first and second lead electrodes.

20. The component measuring device of claim 19, wherein said substrate includes a substrate recessed portion opposing said second excitation electrode to define said sealed space, and said substrate recessed portion being larger than said second excitation electrode and aligned with said elastic member recess.

* * * * *